(12) United States Patent
Lessinger et al.

(10) Patent No.: US 8,650,148 B1
(45) Date of Patent: Feb. 11, 2014

(54) TECHNIQUES FOR TEXT CLASSIFICATION

(76) Inventors: Harry Lessinger, Portland, OR (US);
Ronald George Fenili, Enumclaw, WA (US)

( * ) Notice: Subject to any disclaimer, the term of this patent is extended or adjusted under 35 U.S.C. 154(b) by 375 days.

(21) Appl. No.: 12/931,077

(22) Filed: Jan. 25, 2011

(51) Int. Cl.
G06N 5/00 (2006.01)

(52) U.S. Cl.
USPC ............................................ 706/52; 706/45

(58) Field of Classification Search
USPC .................................................... 706/52, 45
See application file for complete search history.

(56) References Cited

PUBLICATIONS

Letrilliart, et al., Reliability of report coding of hospital referrals in primary care versus practice-based coding, European Journal of Epidemiology 16, 2000, pp. 653-659.*

* cited by examiner

*Primary Examiner* — Wilbert L Starks

(57) ABSTRACT

For various purposes, medical reports and other natural-language texts are assigned discrete codes. Different methods of assigning codes, intended to produce the same results, often fail to assign the same code to the same input.

To improve the consistency and accuracy of this coding process and produce a useful, concrete and tangible result, the embodiment of the present invention electronically assigns to each text a code that is selected from candidate codes produced by multiple pre-existing coding processes, automatic and/or manual. Methods are provided for choosing the code that is, by various criteria, considered most likely to be correct because it represents the best compromise between possible alternative codes.

While the disclosure focuses on medical coding procedures, the invention disclosed herein may be applicable and adaptable to classification of texts or other data for various clinical, scientific, or non-scientific applications.

22 Claims, No Drawings

TECHNIQUES FOR TEXT CLASSIFICATION

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND OF THE INVENTION

1. Field of Invention

Accounting firms, insurance companies, research facilities, hospitals, Doctor's offices, and other industries use numeric codes to describe events in a short hand manner. The invention involves the enhancing of the accuracy of these short hand numeric codes.

2. Background of the Invention

For accounting, billing, insurance, research, and other purposes, medical records are assigned discrete numeric codes by human experts or by automatic software. Recent research raises serious doubts about the validity of coding agreement among coding reviews conducted among coder experts. Such is the case with annual Evaluation and Management (E/M) coding audits conducted by coding auditor/experts. This issue is important because E/M codes represent up to 85% of a practice's billing.

THE PROBLEM

Authoritative studies show that even highly skilled coders significantly disagree with each other on the application of Evaluation and Management (E/M) codes. The conclusion is statistically warranted beyond any reasonable doubt.

One study designed to evaluate agreement among coding specialists employed three hundred certified professional coding specialists randomly selected from the active membership of the American Health Information Management Association. Each was given six hypothetical progress notes of office visits. The group assigned Current Procedural Terminology (CPT) E/M codes to each of the progress notes. The coding specialists disagreed with each other in 43 percent of the cases. The study concluded that a substantial disagreement among coding specialists exists in the application of CPT E/M coding guidelines.

In a related study, five certified coding specialists were recruited who each had at least 12 years of coding experience and who had served as faculty in programs to teach proper coding. Each expert was given six progress notes and was asked to assign a CPT E/M code. Only one of the six codes was deemed correct by all the participants. In still another study, the E/M coding practices of eight highly trained research nurses was evaluated and compared. The study looked at 4,137 outpatient visits. Conclusion: The inter-rater reliability among the nurses was only 36 percent.

And in another study, "to determine the reliability of the federal government's E/M coding system." Raymond E. Jackson, Md., and his team of investigators from William Beaumont Hospital System in Royal Oak, Mich., sent emergency department medical records to several coding specialists. Two sets of charts were sent to multiple specialists at four different coding agencies and a third set was sent to several coding specialists within the same coding agency. The coders were not told about codes others had assigned. The study showed poor agreement among coding specialists on codes they assigned to emergency department medical records. In only 15 percent of the cases did coding agencies show complete agreement Dr. Jackson's results were compared to income tax tests conducted by Money Magazine from 1987 through 1997. Brent Asplin, Md., MPH, author of a related editorial in this issue said, "Money sent a hypothetical family's tax return to 46 professional tax preparers and got back 46 different answers, and not a single one was correct." Asplin went on to say, "Jackson's team found that the Medicare coding system was just as prone to inconsistency and disagreement, even when specialists were put to the task."

Disagreement among expert coders arises primarily from differing interpretations of vague and sometimes ambiguous coding guidelines. CPT coding guidelines appear to be too complex and subjective to be applied consistently even by skilled coding specialists. For example, the medical decision making guidelines give no help in defining the meaning of terms like minimal, limited, and extensive when applied to multiple diagnoses and management options. The studies cited above expose a fundamental flaw in how E/M coding accuracy is measured. Yet the conclusions of single auditors as to the accuracy of codes are continually accepted.

Coding problems resemble real estate appraisal problems. In estimating the market value of a piece of land, five real-estate appraisers will generally come up with five different figures. In addition to the idiosyncrasies of different appraisers, the extent of dispersion around the mean will depend on the uniqueness of a particular property. The more unique the property the wider the dispersion. The medical codes of patients and their treatments have similar variability.

Attempts have been made to measure coding accuracy by comparison of national coding patterns that contained Centers for Medicare & Medicaid Services [formerly known as Medicare] (CMS) national claims and nationwide database averages. Due to differences in doctor and patient populations, comparison with broad averages is probably untenable. Some clinics see younger patients with acute rather than chronic illnesses. Some may have high-volume practices, which result in less thorough documentation and lower-level codes. Some will probably be new to the practice and will bill higher levels of service to get to know their patients. Some might elect to use preexisting templates of the notes, which may produce documentation supporting a higher level of service. Some might see a relatively high number of elderly patients with chronic illnesses. Finally, varying levels of coding expertise may have been involved in the coding.

No doubt exists that the issue of coding audits must be resolved. If audited, variances in billed E/M codes may be discovered, denials or refunds requests may be made and even fines or penalties imposed. Physicians may be barred from Medicare or other third party payer participation. To maintain a profitable medical practice it is of the utmost importance to have accurate billable codes. Accurate audits are also essential for quality assessment, research, public health reporting, and strategic planning.

Documentation standards may be re-written to make coding more objective. How the standards should be written has been the subject of vigorous debate in the American Medical Association and CMS. Nothing concrete has yet been published. An option that is too often practiced in particularly by CMS auditors without formal recognition is the acceptance of codes believed to be no more than one level off of the correct code and in the correct code family. The practice is not actually recorded anywhere.

While no single auditor can provide a benchmark by which to audit individual coders, the mathematical average of, say, 30 unbiased, non-communicating, auditors can offer a more valid basis for judgment.

In summary, a valid picture of coding performance is not evident. In the end, coders are forced to rely on data of questionable usefulness for bench marking, quality assessment, research, public health reporting, and strategic planning.

THE SOLUTION

Accordingly, a method is needed to implement the objectives of medical coding described above.

The key idea of the present invention is to assign codes by any number of different means (human or automatic, currently existing or yet to be invented) and then resolve disputes among coders automatically by computer. Thus, multiple codes assigned by different methods—each with its own chances of being correct in particular situations—can be combined and the best candidate code can be chosen automatically.

OBJECTIVES AND ADVANTAGES

The objectives and advantages of the present invention are:
(a.) improving the result of the coding process by using multiple coding methods including, potentially, methods yet to be developed to obtain codes that appear to describe a particular instance of a medical service, called "candidate codes";
(b.) improving the results of the coding process and further recognizing that more than one interpretation of the same coding parameters exist as the parameters apply to the any given note, closely related notes or text classification system depending on the type of coder or coders involved;
(c.) improving the result of the coding process with the assignment of a series of "candidate codes" reflecting the multiple interpretations;
(d.) improving the result of the coding process by taking an average of the "candidate codes" as elsewhere described in the body of this application to determine the one single most reliable code that applies in each case;
(e.) improving the result of the coding process by improving the quality of the coding so that the code is more reliable, more certain and more likely to be within one confidence interval of the elusive "gold standard";
(f.) improving the result of the coding process by lessening the need for expensive human auditors because the auditing mechanism is already pre-built into the coding software;
(g.) improving the result of the coding process due to the ability of the software to code complex cases;
(h.) improving the result of the coding process by coding based on multiple coding expert points of view and interpretations of the coding guidelines;
(i.) improving the result of the coding process by mimicking the thinking of multiple coder experts so that when the software is run it's as if multiple coding experts are applying their unique and seasoned coding knowledge and expertise to the same note, unlike the current computer assisted coding (CAC) application process in which the CAC software learns from the way the expert coders coded sample notes, then applies the learned knowledge to a review of other similar notes;
(j.) improving the result of the coding process by combining different codes because the use of all data points achieves a better result with more codes assigned to the average, with more stable results that are better than any one of the codes. By combining the different codes achieved by the coders and machines and combining them, the final result is stronger than any one of the data points. Candidate codes are obtained by having the same medical service coded by any combination of human coders, different computer programs that perform coding, and/or a single computer program that performs the coding by using multiple methods, rule sets, knowledge bases, or parameters. A number of methods by which codes can be combined exist as described above. This invention comprises combining codes by any method;
(k.) improving the result of the coding process by uniform and consistent application of the coding guidelines across all of the multiple CAC sub programs as opposed to a single human coders who have been known to code even the same visit multiple ways.

SUMMARY OF THE INVENTION

The invention pertains to methods of assigning a code to a medical report or other text classification by first using multiple existing coding technologies, manual and computerized to assign potential or candidate codes to it, and then using a new computational process to choose the most accurate or most preferred code.

To improve the consistency and accuracy of this coding process, the embodiment of the present invention electronically assigns to each text a code that is selected from candidate codes produced by multiple pre-existing coding processes, automatic and/or manual. Methods are provided for choosing the code that is, by various criteria, considered most likely to be correct because it represents the best compromise between possible alternative codes.

We claim:

1. A method to produce a result, embodied in a digital computer, of processing an electronic representation of a data structure comprising one or more data elements representing the contents of existing medical reports or other texts to be classified by assigning and electronically outputting a collection of one or more discrete codes for each medical report or other text, such report or text being either a single document, or a group of closely related documents pertaining to a single case, comprising the steps of:
   (a) obtaining multiple candidate codes for a report that represent attempts to code the same report using the same system of codes using different coding methods, which can comprise coding done by humans and by computers;
   (b) using statistical methods to choose the best candidate code;
   (c) using statistical methods to quantify the dispersion otherwise stated as disagreement among the candidate codes;
   (d) outputting or storing an electronic representation of the chosen candidate code and of the dispersion (disagreement).

2. Method of claim 1 wherein weights are assigned to candidate codes and these are used in computing measures of central tendency and dispersion.

3. Method of claim 1 wherein central tendency is computed, but not dispersion.

4. The method of claim 1 wherein the means for determining a chosen candidate code is to choose the code most frequently appearing in a collection of candidate codes, a method also known as "voting."

5. The method of claim 1 wherein the means for determining a chosen candidate code is to choose the code with the highest weighted frequency, wherein the highest weighted frequency is obtained by multiplying the number of times each code occurs in a collection of candidates by a weight assigned to that code, a method known as "weighted voting."

6. The method of claim 1 wherein the means for determining a chosen candidate code is that the candidate codes for the report or text are arranged in an ordinal sequence and the chosen candidate code is the median.

7. The method of claim 1 wherein the collection of candidate codes is obtained by any combination comprising the steps of:
   (a) One or more human medical or text classification coders, each coding the same text once or more than once;
   (b) Multiple computer programs or software packages;
   (c) One or more single computer programs operating with multiple rule sets, knowledge bases, parameters, or values of stochastic variables, otherwise known as random variables, and thus producing multiple candidate codes.

8. The method of claim 1 wherein the means for determining the dispersion is to count the number of different candidate codes in the collection of candidate codes in which any code may appear more than once.

9. The method of claim 1 wherein the means for determining the dispersion is to compute the total number of different candidate codes divided by the total number of codes in the collection of candidate codes in which any code may appear more than once.

10. The method of claim 1 wherein the means for determining dispersion is to count the number of different codes in the collection of candidate codes that do not agree with the preferred one.

11. The method of claim 1 wherein the means for determining the dispersion is to compute the number of different codes in the collection of candidate codes that do not agree with the preferred one, divided by the number of different codes in the whole collection.

12. The method of claim 1 wherein the means for determining dispersion is to count the total number of codes in the candidate collection that do not agree with the preferred one, counting a code more than once if it occurs more than once.

13. The method of claim 1 wherein the means for determining dispersion is to count the total number of codes in the candidate collection that do not agree with the preferred one, divided by the total number of codes in the collection, in both cases counting a code more than once if it occurs more than once.

14. The method of claim 1 wherein the codes are arranged in an ordinal sequence and the means of calculating the dispersion is to count the number of steps from one end of the candidate collection to the other end according to this ordinal sequence.

15. The method of claim 1 wherein codes are arranged in an ordinal sequence and dispersion is measured by any statistical measure of dispersion of ordinal data.

16. The method of claim 1 wherein the codes are assigned coordinates in N-dimensional space and dispersion is measured as standard deviation, variance, or any other statistical measure of dispersion in N-dimensional space.

17. The method of claim 1 wherein part or all of the process is implemented by use of a computer readable medium comprising a computer program code configured to cause a processor to execute one or more functions on a conventional Von Neumann or Harvard architecture, superscalar, vector, multi-core, multi-CPU, parallel, or quantum computer, or over a distributed networked application.

18. A method to produce a result, embodied in a digital computer, of processing an electronic representation of a data structure comprising one or more data elements representing the contents of existing medical reports or other texts to be classified by assigning and electronically outputting a collection of one or more discrete codes for each medical report or other text, such report or text being either a single document, or a group of closely related documents pertaining to a single case, comprising the steps of:
   (a) Assigning measures or indications of distance that discloses dissimilarity between candidate codes;
   (b) Assigning coordinates in N-dimensional space, for any suitable N, to the candidate codes on the basis of these distances, and
   (c) The chosen candidate is the discrete code that most nearly matches the mean, median, centroid, medoid, or other measure of central tendency of the candidate codes in appropriately dimensioned space.

19. The method of claim 18 wherein the nearness of match of the candidate codes is judged by linear distance, by least squares, or by other mathematical similarity measures.

20. The method of claim 18 wherein the step of determining the distances includes a step carried out by determining the nearness of each pair of candidate codes in a multi-branched, tree-like, classification structure.

21. The method of claim 18 wherein the step of assigning coordinates or positions includes a step carried out by multi-dimensional scaling in any number of dimensions.

22. The method of claim 18 wherein part or all of the process is implemented by use of a computer readable medium comprising a computer program code configured to cause a processor to execute one or more functions on a conventional Von Neumann or Harvard architecture, superscalar, vector, multi-core, multi-CPU, parallel, or quantum computer, or over a distributed networked application.

\* \* \* \* \*